US00PP33213P3

(12) United States Plant Patent
Sullivan

(10) Patent No.: US PP33,213 P3
(45) Date of Patent: Jun. 29, 2021

(54) ***CANNABIS* PLANT NAMED 'HONEY H-2018'**

(50) Latin Name: *Cannabis sativa*
Varietal Denomination: Honey H-2018

(71) Applicant: MJ Brain Bank, LLC, Denver, CO (US)

(72) Inventor: Kevin Sullivan, Broomfield, CO (US)

(73) Assignee: MJ Brain Bank, LLC, Denver, CO (US)

( * ) Notice: Subject to any disclaimer, the term of this patent is extended or adjusted under 35 U.S.C. 154(b) by 34 days.

(21) Appl. No.: 16/501,982

(22) Filed: Jul. 15, 2019

(65) Prior Publication Data

US 2021/0022280 P1 Jan. 21, 2021

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 226, 263.1
CPC ... A01H 5/02; A01H 5/12; A01H 5/00; A01H 6/28; A61K 36/185
See application file for complete search history.

(56) References Cited

PUBLICATIONS

Frank. The *Cannabis* Female Flower from O'Shaughnessy's Winter 2018/19, retrieved on Nov. 10, 2020, retrieved from the Internet at https://beyondthc.com/the-cannabis-female-flower/, 4 pp. (Year: 2019).*
Spitzer-Rimon et al. Architecture and Florogenesis in Female *Cannabis sativa* Plants Frontiers in Plant Science vol. 10, Article 350 (2019) pp. 1-11. (Year: 2019).*

* cited by examiner

*Primary Examiner* — June Hwu
(74) *Attorney, Agent, or Firm* — Kilpatrick Townsend & Stockton LLP

(57) ABSTRACT

'Honey H-2018' is new *Cannabis* plant variety that has a combination of beneficial characteristics that include high potency, sweet aroma, greater tolerance for fungal diseases, and high vigor.

4 Drawing Sheets

Genus and species: The *Cannabis* variety of this invention is botanically identified as *Cannabis sativa.*

Variety denomination: The variety denomination is 'Honey H-2018'.

BACKGROUND OF THE INVENTION

The invention refers to a new plant variety of *Cannabis* (*Cannabis sativa*) named 'Honey H-2018'. The new *Cannabis* variety is product of a planned and controlled breeding program for new *Cannabis* varieties. The objective of the breeding program is to select new *Cannabis* varieties with a combination of desired vigor, potency, aroma, bud structure/form, yield, and tolerance or resistance to fungal diseases.

The new *Cannabis* variety is a product of a planned breeding program intended to combine some of the desirable characteristics of two existing varieties: G-13x Hashplant (a.k.a., "Retro Boogie") (*Cannabis indica*) and SFV OG Kush x Jack's Cleaner 2 (a.k.a., "Long Bottom Leaf") (*Cannabis sativa*). The variety arose from a cross between the parental varieties; using Long Bottom Leaf as the pollen donor. The parental cross was made in April 2017. Single plants were selected and reproduced by cuttings using traditional horticultural plugs, trays and domes. One of the reproduced plants showed pronounced vigor and was selected as and named 'Honey H-2018'. This plant was transferred to the production on July 2017 and has been asexually reproduced by cuttings since that time. The distinctive characteristics of the variety are stable through successive generations.

The plant was asexually reproduced in Denver, Colo. For asexual reproduction, axillary branches of the plant were excised from the mother plant. The cuttings were treated with indole 3 butyric acid; the cuttings were allowed to root over a period of three weeks at a temperature of 77 degrees F., relative humidity of 60%-80% and constant illumination at an intensity of 100 PPFD.

BRIEF SUMMARY OF THE INVENTION

The following traits have been repeatedly observed and are determined to be unique characteristics of 'Honey H-2018' which in combination distinguish this *Cannabis* plant as a new and distinct variety, as compared to the parents, the closet varieties:

1. The new variety has higher potency as compared to the parents, the closest varieties.
2. The new variety has a sweet aroma as compared to the earthy or spicy aroma in the parents.
3. The new variety has a greater tolerance for fungal diseases such as powdery mildew.
4. The new variety has more vigor as compared to the parents, the closest varieties.

The traits of the new variety was tested at 2600 West Barberry Pl. Denver, Colo., U.S.A.

BRIEF DESCRIPTION OF THE PHOTOGRAPHS

The accompanying photographs illustrate the appearance of the new *Cannabis* variety when the plants were at 63 days after flower initiation. The colors in the photographs are depicted as nearly true as is reasonably possible to obtain in colored reproductions of this type. Colors as shown in the photographs may differ slightly from the color values cited in the detailed botanical description.

DETAILED BOTANICAL DESCRIPTION

Figure 1:
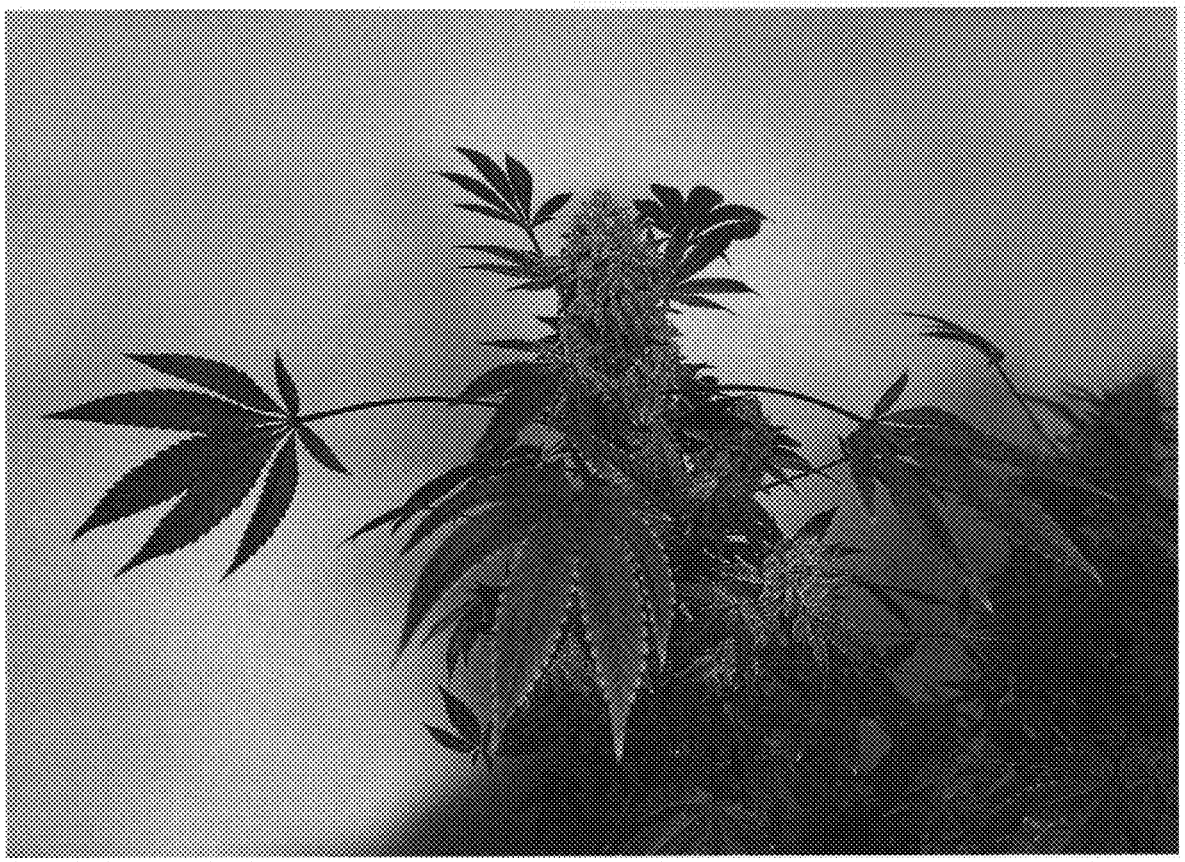
FIG. 1 shows a branch of a plant of the new variety.
Figure 2:
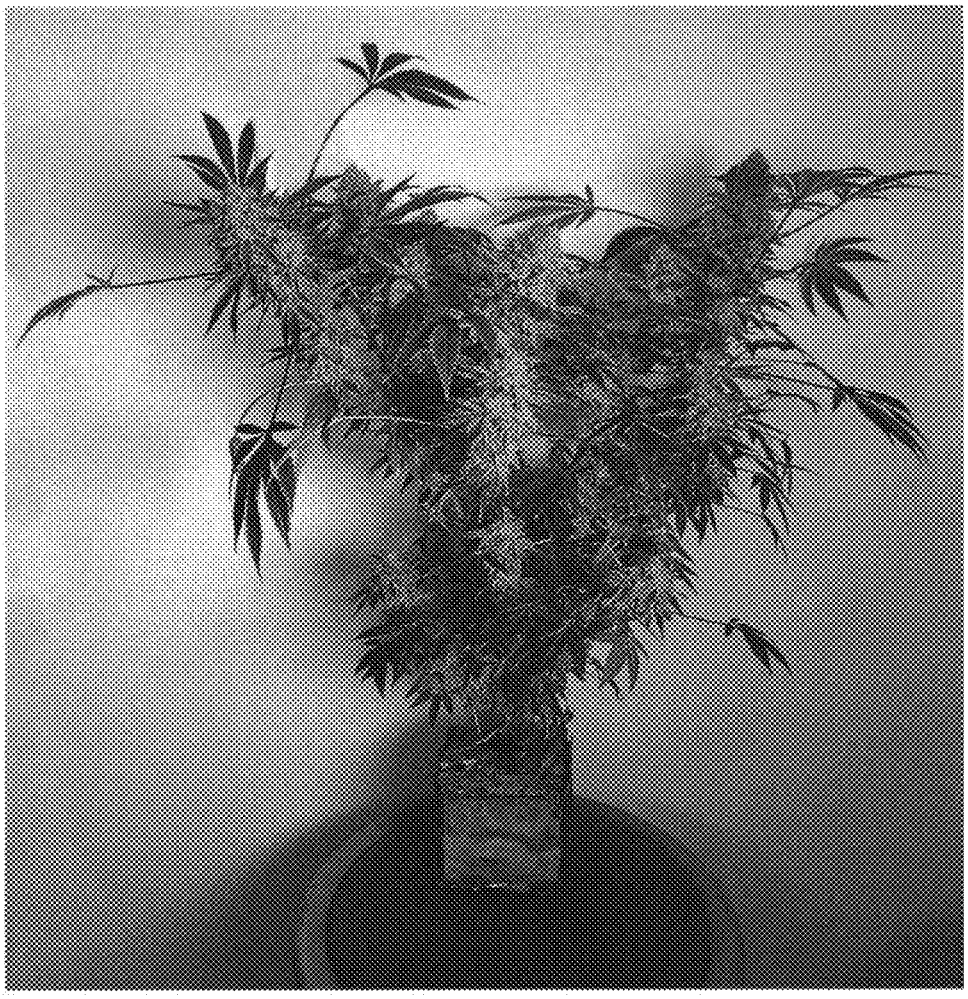
FIG. 2 shows a single plant of the new variety.
Figure 3:
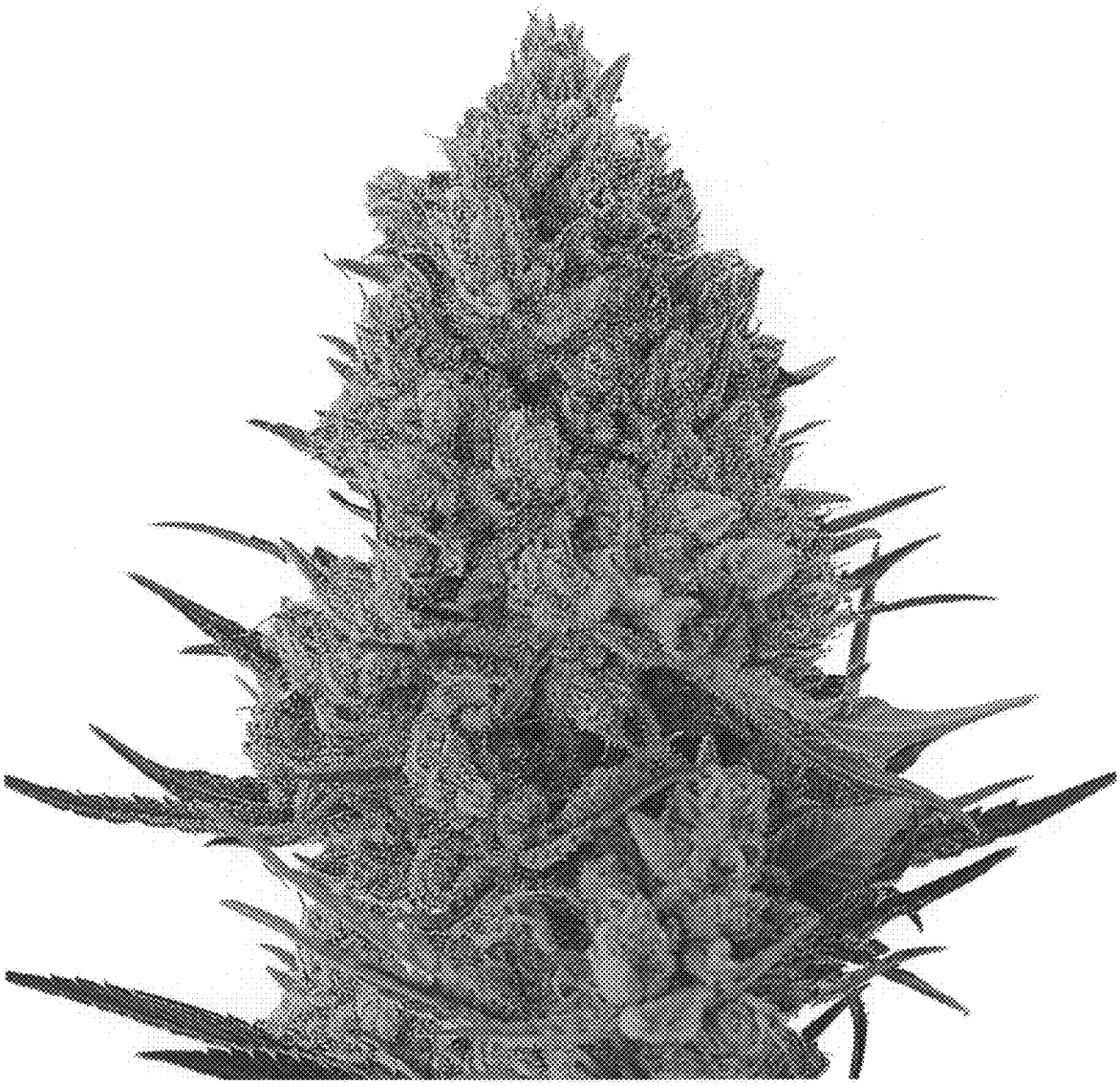
FIG. 3 shows flowers of a plant of the new variety.
Figure 4:
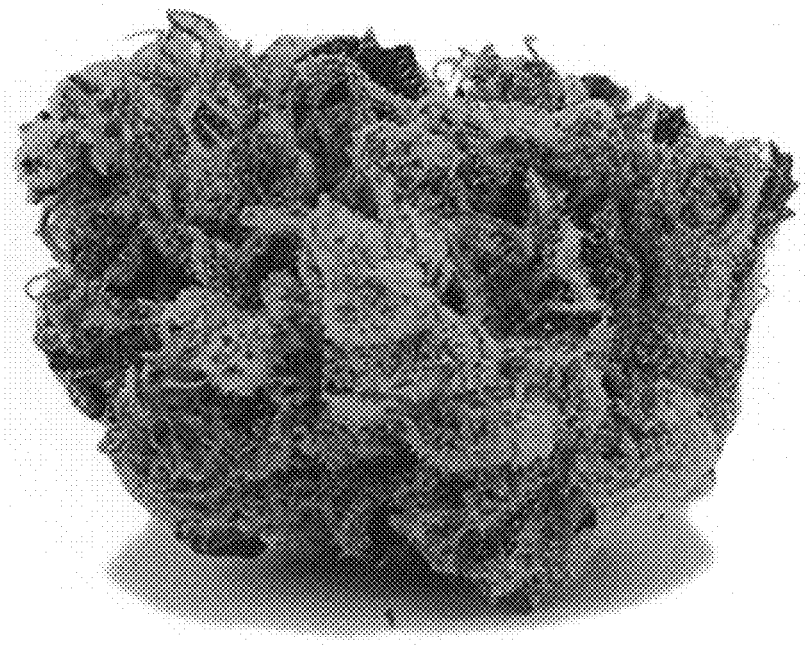
FIG. 4 shows a dried bud of a plant of the new variety.

The following description is based on observations made in February of 2016 on plants produced according to an ordinary growth cycle. However, the new *Cannabis* variety 'Honey H-2018' has not been observed under all possible environmental conditions. The phenotype of the new variety may vary with variations in environmental conditions such as temperature, light intensity and day length without any change in the genotype of the plant.

The photographs and description are taken from plants grown at the 2600 West Barberry Pl. in Denver, Colo., U.S.A. Following rooting, the cuttings were transplanted into the growth medium, Hydroton®, and were grown for approximately 6 weeks or until roots emerged. The plants were then allowed to grow additional 9 weeks. During growth, all plants were fed and watered with nutrients from the Botanicare® Kind® line. Carbon dioxide concentration was measured and supplemented as required, between 900-1500 ppm. Vegetative growth was at a temperature of 78 degrees Fahrenheit, and relative humidity of 45 with constant illumination of 600 PPFD provided by 600 W Metal Halide grow lights. After adequate vegetative growth had been attained, flowering was induced by changing the photoperiod to 12 hours of light and 12 hours of darkness.

Plants were observed on day 63 after the flower induction and the botanical description thereof is provided below. Characteristics described represent those which are typical for the new variety. Measurements and numerical values represent averages for 12 typical plants and plant parts. The actual measurements of any individual plant of plant parts, or any group of plants of plant parts, may vary from the stated averages.

Plant Description

TABLE 1

General

| Characteristic | New Variety | Parental variety (Female plant) | Parental variety (Pollen donor) | Check Variety (*Cannabis Sativa*) |
|---|---|---|---|---|
| Plant life forms | Herbaceous Plant | Herbaceous Plant | Herbaceous Plant | Herbaceous Plant |
| Plant growth habit | Upright, tap-rooted annual plant | Upright, tap-rooted annual plant | Upright, tap-rooted annual plant | Upright, tap-rooted annual plant |
| Plant origin | F1 hybrid between two *Cannabis* Subspecies ((G-13 x Hashplant) x (SFV OG Kush x Jack's Cleaner 2) | F1 *Cannabis* Subspecies (G-13 x Hashplant) | F1 hybrid between two *Cannabis* Subspecies (SFV OG Kush x Jack's Cleaner 2) | F1 hybrid between two *Cannabis* Subspecies (Lambs Bread x Sour Diesel) |

TABLE 1-continued

General

| Characteristic | New Variety | Parental variety (Female plant) | Parental variety (Pollen donor) | Check Variety (*Cannabis Sativa*) |
|---|---|---|---|---|
| Plant propagation | Asexual | Asexual | Asexual | Asexual |
| Propagation ease | Easy[1] | Easy | Moderate[2] | Moderate |
| Height (Unit: m or cm) | Variable; 1 meter | Variable; 1 meter | Variable; 1 meter | Variable; 1 meter |
| Width (Unit: m or cm) | Variable; 0.75 meters | Variable; 0.75 meters | Variable; 0.75 meters | Variable; 0.75 meters |
| Plant vigor | High | High | Medium | High |
| Time to Harvest (Seed to Harvest) | 18-20 weeks | 18-20 weeks | 18-20 weeks | 18-20 weeks |
| Resistance to pests or non-fungal diseases? | No | No | No | No |
| Is this plant a Genetically Modified Organism? | No | No | No | No |

[1]Easy refers to plants that don't require any special products, chemicals or hormones for rooting. Roots will also show up within 10-14 days.

[2]Moderate refers to plants that may take 14-21 days with an increase in rooting after additional hormone or nutrient has been introduced.

TABLE 2

Leaf/Foliage

| Characteristic | New Variety | Parental variety (Female plant) | Parental variety (Pollen donor) | Check Variety |
|---|---|---|---|---|
| Leaf arrangement (Phyllotaxy) | Alternate | Alternate | Alternate | Alternate |
| Leaf shape | Palmately compound | Palmately compound | Palmately compound | Palmately compound |
| Leaf structure | Palmately compound | Palmately compound | Palmately compound | Palmately compound |
| Leaf margins | Coarsely serrated pointing towards tip of leaflet | Coarsely serrated pointing towards tip of leaflet | Coarsely serrated pointing towards tip of leaflet | Coarsely serrated pointing towards tip of leaflet |
| Leaf hairs (Presence or absence) | Absence | Absence | Absence | Absence |
| Leaf length with petiole at maturity (Unit: cm) | 20 | 16 | 16 | 18 |
| Petiole length at maturity (Unit: cm) | 12 | 10 | 11 | 12 |
| Stipule length at maturity (Unit: cm) | 1 | 1 | 1 | 1 |
| Stipule shape | Long, bulbous bases with acuminate (tapering concave to apex) shape | Long, bulbous bases with acuminate (tapering concave to apex) shape | Long, bulbous bases with acuminate (tapering concave to apex) shape | Long, bulbous bases with acuminate (tapering concave to apex) shape |
| Number of leaflets | 5-9 | 5-9 | 5-9 | 5-9 |
| Middle largest (longest) leaflet length (Unit: cm) | 8 | 6 | 8 | 8 |

TABLE 2-continued

| Leaf/Foliage | | | | |
|---|---|---|---|---|
| Characteristic | New Variety | Parental variety (Female plant) | Parental variety (Pollen donor) | Check Variety |
| Middle largest (longest) leaflet width (Unit: cm) | 2 | 2 | 2 | 2 |
| Middle largest (longest) leaflet length/width ratio | 4:1 | 3:1 | 4:1 | 4:1 |
| Number teeth of middle leaflet (average) | 12 | 13 | 11 | 13 |
| Leaf (upper side) color (RHS[3] No.) | 141C | 141C | 141C | 141C |
| Leaf (lower side) color (RHS No.) | 143A | 143A | 143A | 143A |
| Leaf glossiness | Medium | Medium | Medium | Medium |
| Vein/midrib shape (general description) | Even, not alternate. Slightly points towards tip just like the serrations | Even, not alternate. Slightly points towards tip just like the serrations | Even, not alternate. Slightly points towards tip just like the serrations | Even, not alternate. Slightly points towards tip just like the serrations |
| Vein/midrib color | Light green (RHS 140B) | Light green (RHS 140B) | Light green (RHS 140B) | Light green (RHS 140B) |
| Aroma (general description) | Sweet | Earthy | Herbal/Spicy | Gas/Fuel, Earthy |

[3]RHS stands for Royal Horticultural Colour Chart, which can be found at: rhscforgfree-.com

TABLE 3

| Stem | | | | |
|---|---|---|---|---|
| Characteristic | New Variety | Parental variety (Female plant) | Parental variety (Pollen donor) | Check Variety |
| Stem shape (general description) | hollow, large, rugose, punctuate, minutely glandular, ribbed with ribs running parallel to stem | hollow, large, rugose, punctuate, minutely glandular, ribbed with ribs running parallel to stem | hollow, large, rugose, punctuate, minutely glandular, ribbed with ribs running parallel to stem | hollow, large, rugose, punctuate, minutely glandular, ribbed with ribs running parallel to stem |
| Stem diameter at base (Unit: cm) | 1.25 | 1 | 1.5 | 1 |
| Stem color (RHS No.) | 144D | 144D | 144D | 144D |

TABLE 4

| Inflorescence (Female/Pistillate Flowers) | | | | |
|---|---|---|---|---|
| Characteristic | New Variety (Female plant) | Parental variety (Female plant) | Parental variety (Pollen donor) | Check Variety |
| Flowering (blooming) habit (General description) | Dioecious. Forms a tall interconnected cola or terminal bud | Dioecious. Forms a tall interconnected cola or terminal bud | Dioecious. Small inflorescences, tightly packed against stem and separated all along plants branches. | Dioecious. |
| Proportion of female plants (50% or less?) | 50% | N/A | N/A | N/A |
| Inflorescence position | Above | Above | Above | Above |
| Flower arrangement | Overlapping* | Overlapping* | Overlapping* | Overlapping* |
| Number of flowers per plant | 240 | 190 | 210 | 200 |
| Flower shape | sessile and are borne in racemes. Each flower has a small green bract enclosing the ovary with two long, slender stigmas projecting well above the bract. And the flower looks urceolate (urn-shaped). | sessile and are borne in racemes. Each flower has a small green bract enclosing the ovary with two long, slender stigmas projecting well above the bract. And the flower looks urceolate (urn-shaped). | sessile and are borne in racemes. Each flower has a small green bract enclosing the ovary with two long, slender stigmas projecting well above the bract. And the flower looks urceolate (urn-shaped). | sessile and are borne in racemes. Each flower has a small green bract enclosing the ovary with two long, slender stigmas projecting well above the bract. And the flower looks urceolate (urn-shaped). |
| Flower (individual pistillate) length (Unit: mm) | 3 | 3 | 3 | 3 |
| Flower (Racemes) diameter (Unit: cm) | 2 | 2 | 1.5 | 2 |
| Bract shape (general description) | Round at the base but tapered towards the tip | Round at the base but tapered towards the tip | Round at the base but tapered towards the tip | Round at the base but tapered towards the tip |
| Bract color (RHS No.) | 142C | 142C | 142C | 142C |
| Calyx shape (general description) | Round | Round | Round | Round |
| Calyx color (RHS No.) | 142C | 142C | 142C | 142C |

TABLE 4-continued

| Inflorescence (Female/Pistillate Flowers) | | | | |
|---|---|---|---|---|
| Characteristic | New Variety (Female plant) | Parental variety (Female plant) | Parental variety (Pollen donor) | Check Variety |
| Stigma shape (general description) | Curved and wavy, thin | Curved and wavy, thin | Curved and wavy, thin | Curved and wavy, thin |
| Stigma length (Unit: cm) | 0.6 | 0.6 | 0.6 | 0.6 |
| Stigma color (RHS No.) | closely resembling an off white or NN155D | closely resembling an off white or NN155D | closely resembling an off white or NN155D | closely resembling an off white or NN155D |
| Trichome shape (general description) | Glandular, thus it has a stalk that supports secretory head | Glandular, thus it has a stalk that supports secretory head | Glandular, thus it has a stalk that supports secretory head | Glandular, thus it has a stalk that supports secretory head |
| Trichome color (RHS No.) | Mature cap = N172C Stalk = Clear/ Translucent closely resembling an off white or NN155D | Mature cap = N172C Stalk = Clear/ Translucent closely resembling an off white or NN155D | Mature cap = N172C Stalk = Clear/ Translucent closely resembling an off white or NN155D | Mature cap = N172C Stalk = Clear/ Translucent closely resembling an off white or NN155D |
| Terminal bud shape (general description) | Rounded top buds with slightly fox tailing | Large inter-connected cola or terminal bud. Conical | Small, rounded and slightly flat on top. | Round but with textured projections (fox tails). Spikey |
| Terminal bud color (RHS No.) | 142C | 142C | 142C | 142C |
| Pedicel (Presence or absence) | absence | absence | absence | absence |
| Staminate shape | N/A | N/A | Round sacks of modular composition like the hand of a banana but originating from a set of stems similar to grapes | N/A |
| Pollen description | N/A | N/A | Typical yellow pollen with musty smell | N/A |
| Seed description | Starts off white and turns to Brown with black or dark brown stripes | Starts off white and turns to Brown with black or dark brown stripes | N/A | Starts off white and turns to Brown with black or dark brown stripes |
| Petal description | absence | absence | absence | absence |

TABLE 4-continued

| Inflorescence (Female/Pistillate Flowers) | | | | |
|---|---|---|---|---|
| Characteristic | New Variety (Female plant) | Parental variety (Female plant) | Parental variety (Pollen donor) | Check Variety |
| Tetra-hydrocan-nabinolic acid (THC) content** | 25-28% THC | 22-24% THC | N/A (male) | 20-24% THC |

*overlapping refers to the stacking of the bud structure.

**THC content was determined using High Performance Liquid Chromatography ("HPLC") with Diode-Array Detection ("DAD").

TABLE 5

| Other Characteristics and culture | | | | |
|---|---|---|---|---|
| Characteristic | New Variety (Female plant) | Parental variety (Female plant) | Parental variety (Pollen donor) | Check Variety |
| Time period and condition of flowering/ blooming | Blooms in 9-11 weeks after cutting-and-rooting when more than 12 hours light is applied to induce flowering | Blooms in 9-11 weeks after cutting-and-rooting when more than 12 hours light is applied to induce flowering | Blooms in 9-11 weeks after cutting-and-rooting when more than 12 hours light is applied to induce flowering | Blooms in 9-11 weeks after cutting-and-rooting when more than 12 hours light is applied to induce flowering |
| Hardiness of plant[5] | High | High | Medium | Medium |
| Breaking action[4] | High | High | Medium | Medium |
| Rooting rate after cutting/cloning (under certain or specific condition) | 9 days | 9 days | 9 days | 9 days |

[4]refers to how strong the stem is against the breakage such as fibrous, strong, flexible, resistant to breakage, etc.

[5]A high hardiness refers to drought resistant; low nutrient requirement/demand; wind resistant due to strong branching and turgidity, along with above average rooting ability (anchoring).

Additional Characteristics

The plant has high vigor. As one example, 1,750.8 lbs of usable plant matter were harvested in 2020, of which 1,311.1 lbs were bud and 439.7 lbs were trim.

Main stem grooves are shallow. Internode length is medium. Average terminal bud size is medium (4"-5"). Aroma is spicy and floral, with a hint of musk. Flowers are light green, lime, orange, or white.

Shipping quality: This strain can be stored for 6 months prior to final packaging. Plant materials can be used include, for example, raw flower, prerolled joints. Plant materials can also be used in concentrates.

Average width of the leaf is 4.5". Fragrance is a mix of creeping thyme and tricolor sage. Petiole surface is punctuated with farinose trichomes. Stipule's surface is glabrous. Anthocyanin coloration on the petiole—very strong. Stipule's color is green.

Average size of bract is ¼ inch and the average size of bracteoles is ¼ inch.

Trichomes are clear, begin to turn translucent/milky white around day 50 of flowering stage.

Types of glandular trichomes include a) Bulbous, b) Capitate-sessile, and c) Capitate-stalked. Types of non-glandular trichomes present include a) Cystolith hairs and b) Tear-drop shaped.

What is claimed is:

1. A new and distinct variety of *Cannabis* plant named 'Honey H-2018' having the characteristics substantially as described and illustrated herein.

* * * * *